United States Patent [19]

Chou et al.

[11] Patent Number: 4,602,109

[45] Date of Patent: Jul. 22, 1986

[54] NOVEL PESTICIDAL PHENOXYPHENYL AND PHENOXYPYRIDYL BENZOYL UREAS AND PROCESS FOR PREPARATION

[75] Inventors: David T. Chou; John A. Durden, both of Raleigh; Themistocles D. J. D'Silva, Chapel Hill, all of N.C.

[73] Assignee: Union Carbide Corporation, Danbury, Conn.

[21] Appl. No.: 686,735

[22] Filed: Dec. 27, 1984

Related U.S. Application Data

[62] Division of Ser. No. 454,849, Dec. 30, 1982, Pat. No. 4,540,578.

[51] Int. Cl.[4] ............... C07C 143/833; C07C 157/125; C07C 127/22
[52] U.S. Cl. ......................................... 564/23; 564/44
[58] Field of Search ............... 564/44, 23; 260/456 A; 514/594, 518

[56] References Cited

U.S. PATENT DOCUMENTS

| | | | |
|---|---|---|---|
| 3,748,356 | 7/1973 | Wellinga et al. | 260/553 E |
| 3,992,553 | 11/1976 | Sirrenberg et al. | 424/304 |
| 4,013,717 | 3/1977 | Wellinga et al. | 564/44 |
| 4,041,177 | 8/1977 | Sirrenberg et al. | 424/322 |
| 4,148,902 | 4/1979 | Rigterink | 424/266 |
| 4,173,637 | 11/1979 | Nishiyama et al. | 424/263 |
| 4,173,638 | 11/1979 | Nishiyama et al. | 424/263 |
| 4,276,310 | 6/1981 | Sirrenberg et al. | 564/23 |

FOREIGN PATENT DOCUMENTS

| | | | |
|---|---|---|---|
| 57888 | 8/1982 | European Pat. Off. | 564/44 |
| 2083360 | 9/1981 | United Kingdom . | |

Primary Examiner—Charles F. Warren
Assistant Examiner—Roberta A. Picard
Attorney, Agent, or Firm—Gerald L. Coon

[57] ABSTRACT

Novel phenoxyphenyl and phenoxypyridyl benzoyl ureas and a process for their preparation are provided. The novel ureas are useful as the active toxicant in pesticidal compositions.

22 Claims, No Drawings

NOVEL PESTICIDAL PHENOXYPHENYL AND PHENOXYPYRIDYL BENZOYL UREAS AND PROCESS FOR PREPARATION

This application is a division of prior U.S. application Ser. No. 454,849, filed Dec. 30, 1982, now U.S. Pat. No. 4,540,578 issued Sept. 10, 1985.

FIELD OF INVENTION

This invention relates in general to novel phenoxyphenyl and phenoxypyridyl benzoyl ureas and to a process for their preparation. In one aspect, this invention relates to benzoyl ureas which are useful as pesticides.

BACKGROUND OF THE INVENTION

Prior to the present invention few benzoyl ureas had been reported in the patent literature as having pesticidal activity. For example, U.S. Pat. No. 3,992,553 which issued on Nov. 16, 1976, and U.S. Pat. No. 4,041,177 which issued on Aug. 9, 1977, both disclosed certain benzoylureido-diphenyl ethers which were indicated to possess insecticidal properties. Similarly, U.S. Pat. Nos. 3,748,356 and 3,933,908 also disclosed certain substituted benzoyl ureas and stated that the compositions had strong insecticidal activity. U.S. Pat. No. 4,148,902 which issued Apr. 10, 1979 discloses substituted ((phenylamino)carbonyl)pyridine carboxamides and claims a method of controlling insects in addition to the compositions themselves. Additional disclosures of benzoyl ureas in the patent literature are found in U.S. Pat. Nos. 4,166,124; 4,083,977; 4,160,834; 4,264,605; 4,064,267; and 4,005,223; 4,123,449; and 4,068,002. Thus prior to the present invention relatively few materials of this class have been claimed to be useful as pesticides.

Accordingly, one or more of the following objects can be achieved by the practice of this invention. It is an object of this invention to provide novel phenoxyphenyl and phenoxypyridyl benzoyl ureas. Another object of this invention is to provide certain benzoyl ureas which exhibit excellent insecticidal activity. A still further object of this invention is to provide novel benzoyl ureas, such as, 1-benzoyl-3-(4-[4-(4-chlorophenylsulfonyl)phenoxy]phenyl)urea, and the like. Another object is to provide processes for the preparation of the novel benzoyl ureas. A further object is to provide novel pesticidal compositions containing the novel benzoyl ureas as the active toxicant. Another object of the invention is to provide a method for controlling pests by the application of the novel pesticidal compositions. These and other objects will readily become apparent to those skilled in the art in the light of the teachings herein set forth.

SUMMARY OF THE INVENTION

In its broad aspect the invention relates to novel phenoxyphenyl and phenoxypyridyl benzoyl ureas, pesticidal compositions containing the same, and processes for their preparation and use. The benzoyl ureas of this invention can be represented by the following formula $\underline{1}$:

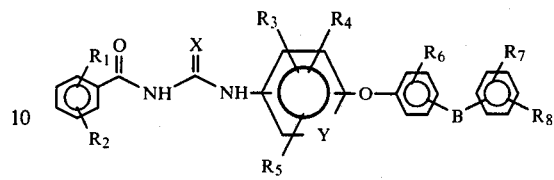

wherein: X, Y, B, $R_1$, $R_2$, $R_3$, $R_4$, $R_5$, $R_6$, $R_7$ and $R_8$ are as hereinafter described.

DETAILED DESCRIPTION OF THE INVENTION

As indicated above, the novel benzoyl ureas of this invention are conveniently represented by the formula:

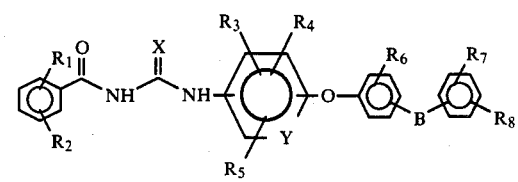

wherein:
X is oxygen or sulfur;
Y is $CR_3$ or nitrogen;
B may be oxygen, sulfur, sulfinyl, sulfonyl, oxysulfonyl, sulfonyloxy or carbonyl;
$R_1$ and $R_2$ are independently hydrogen, halogen, methoxy, alkyl ($C_1$-$C_4$) or trifluoromethyl;
$R_3$, $R_4$, $R_5$ are independently hydrogen, methoxy, halogen, alkyl ($C_1$-$C_4$) or trifluoromethyl;
$R_6$ may be hydrogen, halogen or alkyl ($C_1$-$C_4$) or trifluoromethyl;
$R_7$ and $R_8$ are independently hydrogen, halogen, alkyl ($C_1$-$C_4$), trifluoromethyl, alkylthio ($C_1$-$C_4$), alkylsulfinyl ($C_1$-$C_4$), alkylsulfonyl ($C_1$-$C_4$), or $R_7$ and $R_8$ can optionally be a substituted arylthio, a substituted arylsulfonyl, or a substituted arylsulfinyl, provided that when B is oxygen and Y is $CR_3$, at least two of $R_3$-$R_5$ are other than hydrogen. The optional substituents on $R_7$ and $R_8$ can be alkyl ($C_1$-$C_4$) or halogen.

A preferred class of benzoyl ureas within the above generic formula are the phenoxyphenyl ureas which can be represented by the formula:

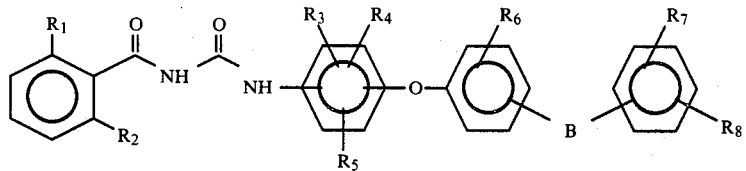

wherein: B is oxygen or $S(O)_n$ wherein n is 0 to 2, and $R_1$-$R_8$ are as previously described.

Another class within the generic formula are the phenoxy pyridyl ureas of the following formula:

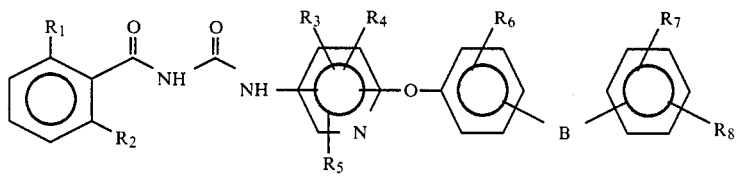

wherein: B and $R_1$–$R_8$ are as indicated above.

A further class encompassed by the generic formula are the ureas represented by the formula:

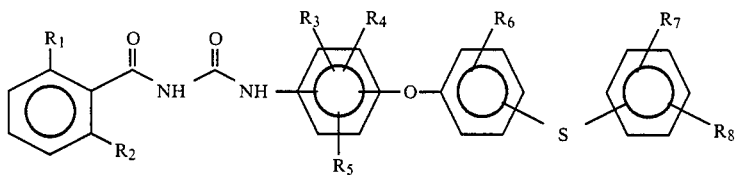

wherein: $R_1$–$R_8$ are as indicated above.

Another preferred class of the phenoxyphenyl ureas are those wherein a phenyl group is joined to the phenoxy group through a sulfonyl linkage:

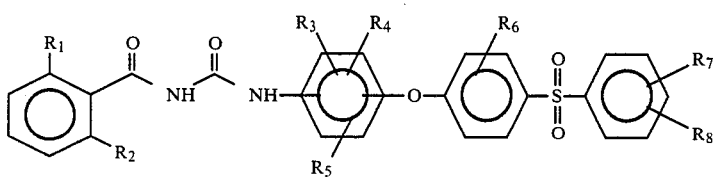

wherein: $R_1$–$R_8$ are as previously described.

The phenoxypyridyl ureas are also a preferred class within the generic formula and can be represented by the following formula:

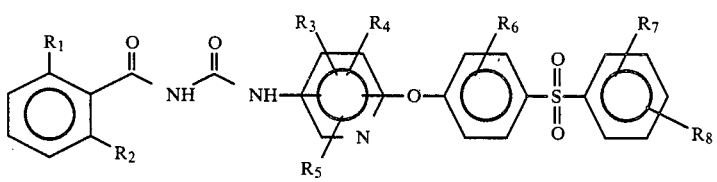

wherein: $R_1$–$R_8$ are as previously indicated.

A preferred class of benzoyl thioureas within the above generic formula are the phenoxyphenyl thioureas which can be represented by the formula:

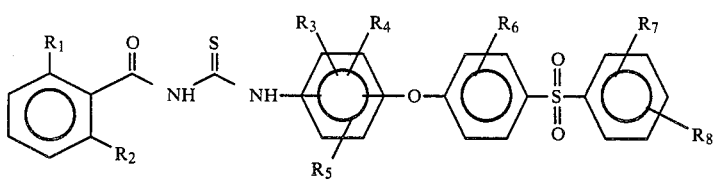

wherein: $R_1$–$R_8$ are previously described.

The novel benzoyl urea compounds disclosed herein are illustrated by, but not limited to, the following:
1-(2,6-dichlorobenzoyl)-3-(3,6-dimethyl-5-chloro-4-[4-(4-chlorophenylsulfonyl)phenoxy]phenyl)urea,
1-(2,6-difluorobenzoyl)-3-(3,6-dimethyl-5-chloro-4-[4-(4-chlorophenylsulfonyl)phenoxy]phenyl)urea,
1-(2-chloro-6-fluorobenzoyl)-3-(3,6-dimethyl-5-chloro-4-[4-(4-chlorophenylsulfonyl)phenoxy]phenyl)urea,
1-(2-chlorobenzoyl)-3-(3,6-dimethyl-5-chloro-4-[4-(4-chlorophenylsulfonyl)phenoxy]phenyl)urea,
1-(2-methylbenzoyl)-3-(3,6-dimethyl-5-chloro-4-[4-(4-chlorophenylsulfonyl)phenoxy]phenyl)urea,
1-(2-trifluoromethylbenzoyl)-3-(3,6-dimethyl-5-chloro-4-[4-(4-chlorophenylsulfonyl)phenoxy]phenyl)urea,
1-(2,6-dichlorobenzoyl)-3-(3,5-dimethyl-4-[4-(4-chlorophenylsulfonyl)phenoxy]phenyl)urea,
1-(2,6-difluorobenzoyl)-3-(3,5-dimethyl-4-[4-(4-chlorophenylsulfonyl)phenoxy]phenyl)urea,
1-(2-chloro-6-fluorobenzoyl)-3-(3,5-dimethyl-4-[4-(4-chlorophenylsulfonyl)phenoxy]phenyl)urea,
1-(2-chlorobenzoyl)-3-(3,5-dimethyl-4-[4-(4-chlorophenylsulfonyl)phenoxy]phenyl)urea,
1-(2,6-dichlorobenzoyl)-3-(3,6-dimethyl-5-chloro-4-[4-(4-chlorophenylsulfenyl)phenoxy]phenyl)urea,
1-(2,6-difluorobenzoyl)-3-(3,6-dimethyl-5-chloro-4-[4-(4-chlorophenylsulfenyl)phenoxy]phenyl)urea,
1-(2-chloro-6-fluorobenzoyl)-3-(3,6-dimethyl-5-chloro-4-[4-(4-chlorophenylsulfenyl)phenoxy]phenyl)urea, 1-(2-chlorobenzoyl)-3-(3,6-dimethyl-5-chloro-4-[4-(4-chlorophenylsulfenyl)phenoxy]phenyl)urea, 1-(2-chlorobenzoyl)-3-(3,6-dimethyl-5-chloro-4-[4-(4-chlorophenylsulfenyl)phenoxy]phenyl)thiourea, 1-(2,6-difluorobenzoyl)-3-(3,6-dimethyl-5-chloro-4-[4-(4-chlorophenylsulfenyl)phenoxy]phenyl)thiourea, 1-(2,6-difluorobenzoyl)-3-(3,6-dimethyl-5-chloro-4-[4-(4-chlorophenylsulfonyl)phenoxy]phenyl)thiourea, 1-(2,6-difluorobenzoyl)-3-(3,6-dimethyl-5-chloro-4-[4-(4-chlorophenylsulfinyl)phenoxy]phenyl)thiourea, 1-(2,6-dichlorobenzoyl)-3-(3,6-dimethyl-5-chloro-4-[4-(4-chlorophenylsulfinyl)phenoxy]phenyl)urea, 1-(2-chloro-6-fluorobenzoyl)-3-(3,6-dimethyl-5-chloro-4-[4-(4-chlorophenylsulfinyl)phenoxy]phenyl)urea, 1-(2-chlorobenzoyl)-3-(3,6-dimethyl-5-chloro-4-[4-(4-chlorophenylsulfinyl)phenoxy]phenyl)urea, 1-(2,6-difluorobenzoyl)-3-(3-trifluoromethyl-4-[4-(4-chlorophenylsulfonyl)phenoxy]phenyl)urea, 1-(2,6-dichlorobenzoyl)-3-(3-trifluoromethyl-4-[4-(4-chlorophenylsulfonyl)phenoxy]phenyl)urea, 1-(2-chloro-6-fluorobenzoyl)-3-(3-trifluoromethyl-4-[4-(4-chlorophenylsulfonyl)phenoxy]phenyl)urea, 1-(2-chlorobenzoyl)-3-(3-trifluoromethyl-4-[4-(4-chlorophenylsulfonyl)phenoxy]phenyl)urea, 1-(2,6-difluorobenzoyl)-3-(3,5-dimethyl-4-[4-(4-chlorophenylsulfinyl)phenoxy]phenyl)urea, 1-(2,6-dichlorobenzoyl)-3-(3,5-dimethyl-4-[4-(4-chlorophenylsulfinyl)phenoxy]phenyl)urea, 1-(2-chloro-6-fluorobenzoyl)-3-(3,5-dimethyl-4-[4-(4-chlorophenylsulfinyl)phenoxy]phenyl)urea, 1-(2-chlorobenzoyl)-3-(3,5-dimethyl-4-[4-(4-chlorophenylsulfinyl)phenoxy]phenyl)urea, 1-(2,6-difluorobenzoyl)-3-(2-[4-(4-chlorophenylsulfonyl)phenoxy]-3-bromo-5-pyridyl)urea 1-(2,6-dichlorobenzoyl)-3-(2-[4-(4-chlorophenylsulfonyl)phenoxy]-3-bromo-5-pyridyl)urea 1-(2-chloro-6-fluorobenzoyl)-3-(2-[4-(4-chlorophenylsulfonyl)phenoxy]-3-bromo-5-pyridyl)urea 1-(2-chlorobenzoyl)-3-(2-[4-(4-chlorophenylsulfonyl)phenoxy]-3-bromo-5-pyridyl)urea 1-(2,6-difluorobenzoyl)-3-(2-[4-(4-chlorophenylsulfonyl)phenoxy]-3-bromo-5-pyridyl)thiourea 1-(2,6-difluorobenzoyl)-3-(2-[4-(4-chlorophenylsulfenyl)phenoxy]-3-chloro-5-pyridyl)urea 1-(2,6-dichlorobenzoyl)-3-(2-[4-(4-chlorophenylsulfenyl)phenoxy]-3-chloro-5-pyridyl)urea 1-(2-chloro-6-fluorobenzoyl)-3-(2-[4-(4-chlorophenylsulfenyl)phenoxy]-3-chloro-5-pyridyl)urea 1-(2-chlorobenzoyl)-3-(2-[4-(4-chlorophenylsulfenyl)phenoxy]-3-chloro-5-pyridyl)urea 1-(2,6-difluorobenzoyl)-3-(2-[4-(4-chlorophenylsulfenyl)phenoxy]-3-chloro-5-pyridyl)thiourea 1-(2,6-difluorobenzoyl)-3-(2-[4-(4-chlorophenylsulfinyl)phenoxy]-3-chloro-5-pyridyl)urea 1-(2,6-dichlorobenzoyl)-3-(2-[4-(4-chlorophenylsulfinyl)phenoxy]-3-chloro-5-pyridyl)urea 1-(2-chloro-6-fluorobenzoyl)-3-(2-[4-(4-chlorophenylsulfinyl)phenoxy]-3-chloro-5-pyridyl)urea 1-(2-chlorobenzoyl)-3-(2-[4-(4-chlorophenylsulfinyl)phenoxy]-3-chloro-5-pyridyl)urea 1-(2,6-difluorobenzoyl)-3-(2-[4-(4-chlorophenylsulfinyl)phenoxy]-3-chloro-5-pyridyl)thiourea 1-(2,6-difluorobenzoyl)-3-(3-chloro-4-[4-(2-chloro-4-trifluoromethylphenylsulfenyl)-phenoxy]phenyl)urea, 1-(2,6-dichlorobenzoyl)-3-(3-chloro-4-[4-(2-chloro-4-trifluoromethylphenylsulfenyl)-phenoxy]phenyl)urea, 1-(2,6-dimethylbenzoyl)-3-(3-chloro-4-[4-(2-chloro-4-trifluoromethylphenylsulfenyl)-phenoxy]phenyl)urea, 1-(2-chlorobenzoyl)-3-(3-chloro-4-[4-(2-chloro-4-trifluoromethylphenylsulfenyl)-phenoxy]phenyl)urea, 1-(2,6-difluorobenzoyl)-3-(3-chloro-4-[4-(2-chloro-4-trifluoromethylphenylsulfenyl)-phenoxy]phenyl)thiourea, 1-(2,6-difluorobenzoyl)-3-(3-chloro-4-[4-(2-chloro-4-trifluoromethylphenylsulfonyl)-phenoxy]phenyl)urea, 1-(2,6-dichlorobenzoyl)-3-(3-chloro-4-[4-(2-chloro-4-trifluoromethylphenylsulfonyl)-phenoxy]phenyl)urea, 1-(2-chlorobenzoyl)-3-(3-chloro-4-[4-(2-chloro-4-trifluoromethylphenylsulfonyl)-phenoxy]phenyl)urea, 1-(2,6-difluorobenzoyl)-3-(3-chloro-4-[4-(2-chloro-4-trifluoromethylphenylsulfonyl)-phenoxy]phenyl)thiourea, 1-(2,6-difluorobenzoyl)-3-(3,6-dimethyl-5-chloro-4-[2-chloro-4-(2,4-dimethylphenoxy)-phenoxy]phenyl)urea, 1-(2,6-dichlorobenzoyl)-3-(3,6-dimethyl-5-chloro-4-[2-chloro-4-(2,4-dimethylphenoxy)-phenoxy]phenyl)urea, 1-(2-chlorobenzoyl)-3-(3,6-dimethyl-5-chloro-4-[3-chloro-4-(2,4-dimethylphenoxy)-phenoxy]phenyl)urea, 1-(2-chloro-6-fluorobenzoyl)-3-(3,6-dimethyl-5-chloro-4-[2-chloro-4-(2,4-dimethylphenoxy)phenoxy]phenyl)urea, 1-(2,6-difluorobenzoyl)-3-(3,6-dimethyl-5-chloro-4-[2-chloro-4-(2,4-dimethylphenoxy)-phenoxy]phenyl)urea, 1-(2,6-dimethoxybenzoyl)-3-(3,6-dimethyl-5-chloro-4-[3-chloro-4-(2,4-dimethylphenoxy)-phenoxy]phenyl)urea, 1-(2,6-difluorobenzoyl)-3-(3,6-dimethyl-5-chloro-4-[2-methyl-4-(2,4-dichlorophenoxy)-phenoxy]phenyl)urea, 1-(2,6-dichlorobenzoyl)-3-(3,6-dimethyl-5-chloro-4-[2-methyl-4-(2,4-dichlorophenoxy)-phenoxy]phenyl)urea, 1-(2-chlorobenzoyl)-3-(3,6-dimethyl-5-chloro-4-[2-methyl-4-(2,4-dichlorophenoxy)-phenoxy]phenyl)urea, 1-(2,6-dimethoxybenzoyl)-3-(3,6-dimethyl-5-chloro-4-[2-methyl-4-(2,4-dimethylphenoxy)-phenoxy]phenyl)urea, 1-(2,6-difluorobenzoyl)-3-(3,6-dimethyl-5-chloro-4-[2-methyl-4-(2,4-dichlorophenoxy)-phenoxy]phenyl)thiourea, 1-(2-chlorobenzoyl)-3-(3,6-dimethyl-5-chloro-4-[3-chloro-4-(2-t-butyl-4-methylphenoxy)-phenoxy]phenyl)urea, 1-(2,6-difluorobenzoyl)-3-(3,6-dimethyl-5-chloro-4-[2-chloro-4-(2-t-butyl-4-methylphenoxy)-phenoxy]phenyl)urea, 1-(2,6-dichlorobenzoyl)-3-(3,6-dimethyl-5-chloro-4-[3-chloro-4-(2-t-butyl-4-methylphenoxy)-phenoxy]phenyl)urea, 1-(2,6-difluorobenzoyl)-3-(3,6-dimethyl-5-chloro-4-[3-isopropyl-4-(2,4-dichlorophenoxy)-phenoxy]phenyl)urea, 1-(2,6-dichlorobenzoyl)-3-(3,6-dimethyl-5-chloro-4-[3-isopropyl-4-(2,4-dichlorophenoxy)-phenoxy]phenyl)urea, 1-(2-chlorobenzoyl)-3-(3,6-dimethyl-5-chloro-4-[2-isopropyl-4-(2,4-dichlorophenoxy)-phenoxy]phenyl)urea, 1-(2-chlorobenzoyl)-3-(3,6-dimethyl-5-chloro-4-[2-isopropyl-4-(2,4-dichlorophenoxy)-phenoxy]phenyl)thiourea, 1-(2-dichlorobenzoyl)-3-(3-chloro-4-[4-(2-chloro-4-t-butylthiophenylsulfonyl)-phenoxy]phenyl)urea, 1-(2,6-difluorobenzoyl)-3-(3,6-dimethyl-5-chloro-4-[4-(4-trifluoromethylphenoxy)phenoxy]phenyl)urea, 1-(2,6-diflurorbenzoyl)-3-(3,5-dichloro-4-[4-(4-chlorobenzoyl)phenoxy]phenyl)urea, 1-Benzoyl-3-(3,5-dichloro-4-[4-(4-chlorophenylsulfonyl)phenoxy]phenyl)thiourea, 1-(2,6-difluorobenzoyl)-3-(3,5-dichloro-4-[2-trifluoromethyl-4-(4-chlorophenylsulfonyl)phenoxy]phenyl)urea, 1-(2,6-diflurobenzoyl)-3-(2-methyl-5-chloro-4-[4-(4-chloro-phenylsulfonyl)phenoxy]phenyl)urea, 1-(2-chlorobenzoyl)-3-(2,5-dimethyl-4-[4-(4-chlorophenylsulfonyl)phenoxy]phenyl)thiourea, 1-(2-chlorobenzoyl)-3-(3-methoxy-4-[4-(4-chlorophenylsulfonyl)phenoxy]phenyl)urea, 1-(2,6-difluorobenzoyl)-3-(3-chloro-4-[4-(2-chloro-4-[4-chlorophenylthio]phenylsulfonyl)-3-methylphenoxy]phenyl)urea, 1-(2,6-difluorobenzoyl)-3-(3-chloro-4-[4-(2-chloro-4-[4-chlorophenylsulfinyl]phenylsulfonyl)phenoxy]phenyl)urea, 1-(2,6-difluorobenzoyl)-3-[3,5-dichloro-4-[4-(4-chlorophenoxysulfonyl)phenoxy]phenyl]urea, 1-(2,6-difluorobenzoyl)-3-[3,5-dichloro-4-[4-(4-chlorophenylsulfonyloxy)phenoxy]phenyl]urea.

1-(2,6-difluorobenzoyl)-3-[2,5-dimethyl-3-chloro-4-[4-(4-chlorophenoxysulfonyl)phenoxy]phenyl]urea, 1-(2-chlorobenzoyl)-3-[2,5-dimethyl-3-chloro-4-[4-(4-chlorophenoxysulfonyl)phenoxy]phenyl]urea.

1-(2,6-difluorobenzoyl)-3-(3-chloro-4-[4-(2-chloro-4-[4-chlorophenylsulfonyl]phenylsulfonyl)phenoxy]phenyl)urea, 1-(2,6-difluorobenzoyl)-3-(3-methyl-4-[4-(4-t-butylsulfinylphenylsulfonyl)phenoxy]phenyl)urea, 1-(2,6-difluorobenzoyl)-3-(3-methyl-4-[4-(4-methylthiophenylsulfonyl)phenoxy]phenyl)urea, 1-(2,6-difluorobenzoyl)-3-(3-methyl-4-[4-(4-methylsulfonylphenylsulfonyl)phenoxy]phenyl)urea, and the like.

The novel compounds of this invention may be prepared by reacting a substituted phenoxyaniline or phenoxyaminopyridine 3 with a benzoylisocyanate or benzoyl isothiocyanate 2 as shown in Scheme I.

SCHEME I

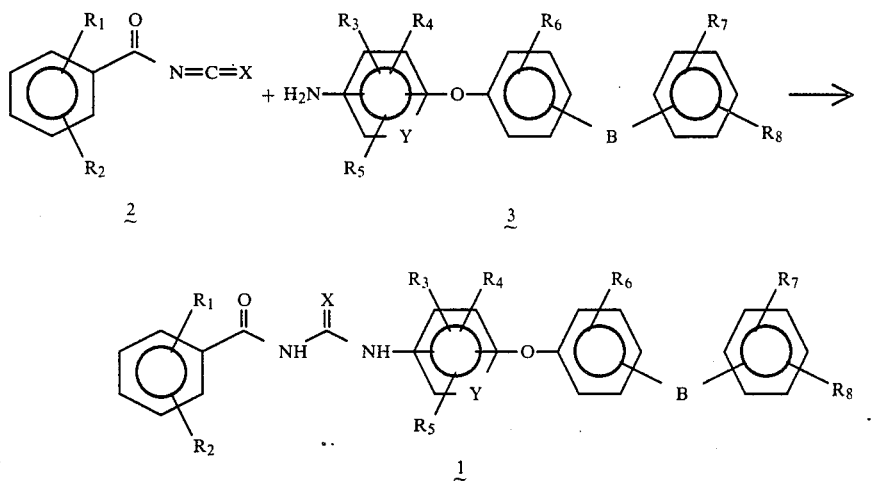

Wherein, X, Y, B, R₁, R₂, R₃, R₄, R₅, R₆, R₇, and R₈ are as previously described.

The novel compounds may also be prepared through the reactions of benzamide 4 with a phenoxyphenylisocyanate(phenoxyphenylisothiocyanate) or phenyoxypyridylisocyanate(phenoxypyridylisothiocyanate) 5 according to Scheme II.

SCHEME II

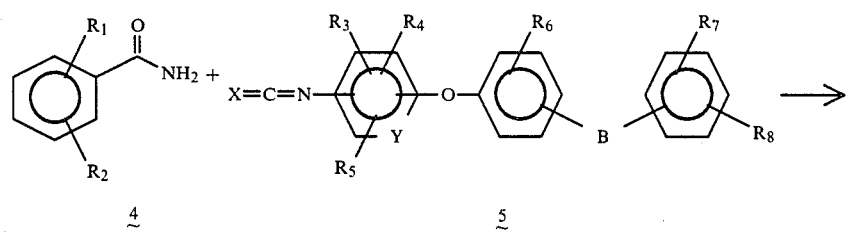

-continued
SCHEME II

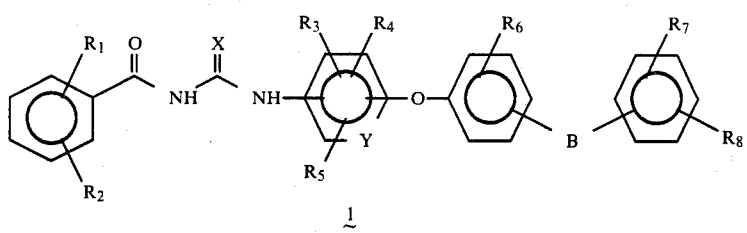

Wherein: X, Y, B, $R_1$, $R_2$, $R_3$, $R_4$, $R_5$, $R_6$, $R_7$, and $R_8$ are previously described.

In general, the reactions illustrated in Schemes I and II proceed smoothly in an organic solvent like aromatic hydrocarbons or halogenated hydrocarbons. Solvents like toluene or 1,2-dichloroethane are preferred. Reaction temperatures are not critical. The temperature may range from 25° to 200° C.

The intermediates shown in Scheme I and II can be prepared according to generally accepted procedures. The substituted benzoylisocyanate 2 can be prepared from the corresponding benzamide 4 following the general procedure of Speziale et. al., *J. Org. Chem.* 27, 3742 (1962).

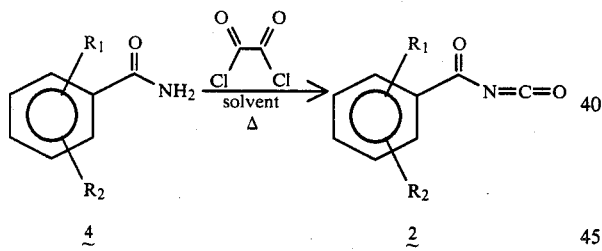

The substituted benzoylisothiocyanate can be prepared in higher yield by the reaction of benzoyl chloride with potassium thiocyanate. Aromatic hydrocarbon or chlorinated hydrocarbon can be used. This procedure, in general, is similar to that of Ambelang, et. al., *J. Am. Chem. Soc.* 61, 632 (1937).

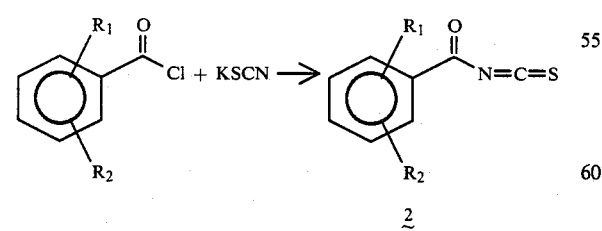

The benzamides of the type 4 are either available commercially or can be obtained following literature procedures.

Anilines of the type 3 can be prepared according to either Scheme III or IV shown below.

SCHEME III

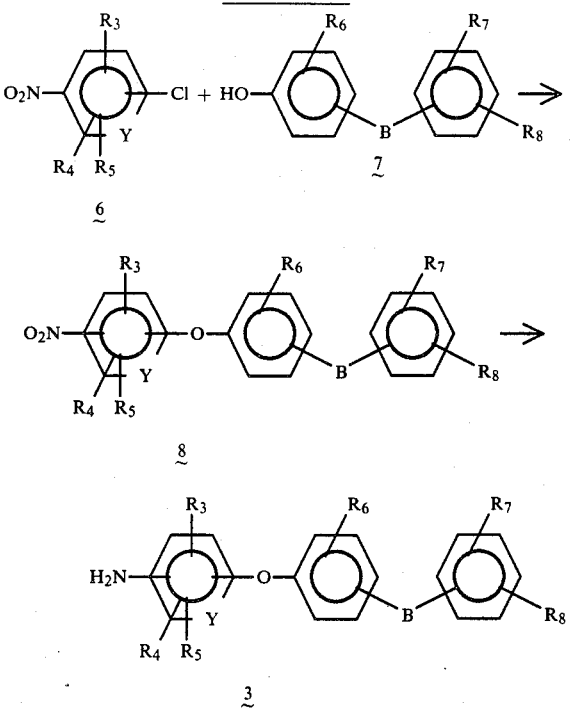

Wherein: Y, B, $R_3$, $R_4$, $R_5$, $R_6$, $R_7$, and $R_8$ are previously described.

SCHEME IV

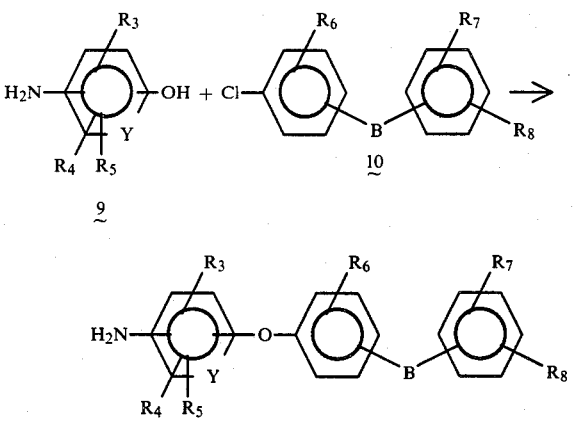

Wherein: Y, B, $R_3$, $R_4$, $R_5$, $R_6$, $R_7$, and $R_8$ are previously described.

The reaction of substituted phenol 7 with chloronitrobenzene or chloronitropyridine 6 to give nitro ether 8 proceeds in the presence of base in an inert solvent at elevated temperatures. The bases suitable for this reaction are potassium carbonate, sodium hydride, potassium hydroxide and sodium hydroxide. Suitable solvents are acetone, toluene, dimethylformamide, and dimethylsulfoxide.

The reduction of nitroether 8 to the aniline 3 can be achieved by hydrogenation using catalytic amount of platinum or palladium on carbon, with pressures ranging from 10–100 PSI at ambident temperature. Suitable solvents for hydrogenation include aromatic hydrocarbon or alcohol. The reduction of nitroether 8 to aniline 3 can also be achieved by chemical method using the procedure of E. Enders, et. al., GB No. 1,456,964.

The reaction of aminophenol 9 with substituted chlorobenzene 10 proceeds in the presence of base in an inert solvent at elevated temperature to give the substituted aniline 3. The bases suitable for this reaction are potassium carbonate, sodium hydride, potassium hydroxide, and sodium hydroxide. Suitable solvents are toluene, acetone, dimethylformamide, and dimethylsulfoxide.

The substituted phenol, substituted chloronitrobenzene, and substituted aminophenol are available commercially or can be prepared using literature procedures.

The intermediate, such as 2-chloro-3-methyl-5-nitropyridine, used for the ether formation reaction, was obtained by the procedure of Hawkins, et al,, *J. Org. Chem.* 14, 328 (1949).

2,3-dichloro-5-nitropyridine was obtained by one sequence shown below:

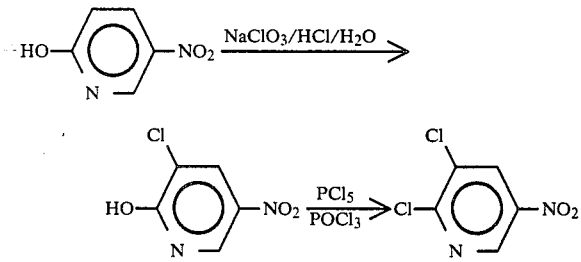

3,5-dimethyl-4-aminophenol, another intermediate, was obtained by the following procedure.

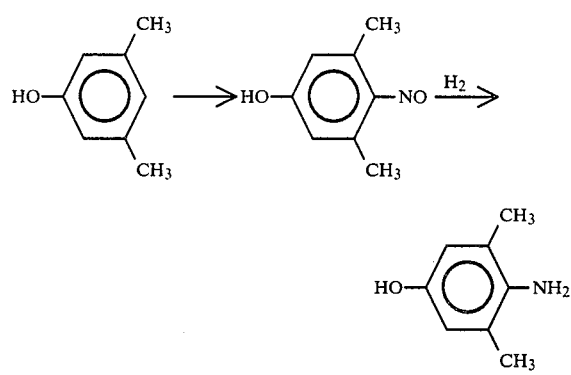

4-(4-chlorophenylsulfonyl)phenol was prepared by selective hydrolysis on one of the chlorine of 4,4'-dichloro-diphenyl sulfone by the procedure of Johnson, et. al., *J. Polym. Ser:* (A-1) 5, 2415 (1967)

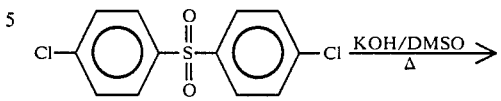

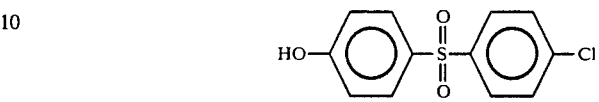

The substituted isothiocyanate and isocyanate 5 can be prepared by the reaction of substituted aniline or aminopyridine 3 with thiophosgene or phosgene.

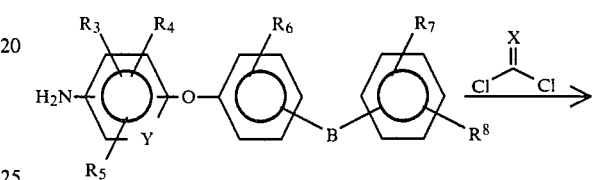

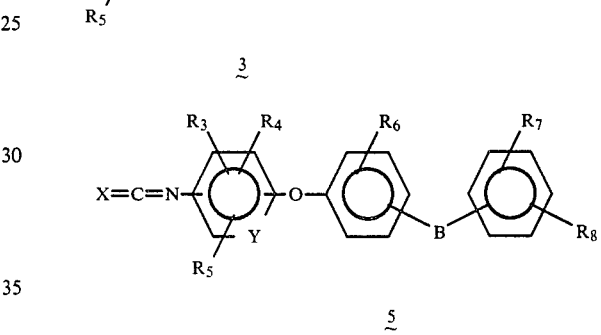

Wherein: X, Y, B, $R_3$, $R_4$, $R_5$, $R_6$, $R_7$, and $R_8$ are previously described.

The compounds contemplated in this invention may be applied as insecticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

Mixtures of the active compounds may be employed if desired as well as combinations of the active compounds of this invention with other biologically active compounds of synergists.

The following examples illustrate the best mode presently contemplated for the practice of the invention:

EXAMPLE 1

Part A: Preparation of 4-(4-[4-chlorophenylsulfonyl]phenoxy)-3,5-dichloronitrobenzene To a 250 mL flask equipped with a condenser, stirrer, under nitrogen atmosphere, was added 3,4,5-trichloronitrobenzene (17.15 g, 0.076 mol), potassium carbonate (10.99 g, 0.080 mol), 4-(4-chlorophenylsulfonyl)-phenol (21.00 g, 0.078 mol), and dimethylformamide (130 mL, dried over 4A molecular sieves). The resulting mixture was heated up to 120° for 4 hours. It was cooled, filtered, and concentrated. This material was chromatographed through florisil column. Elution with hexane/ethylacetate (19/1 to 9/1 ratio) mixture afforded 17.5 g (0.038 mol) of product as a white solid; m.p. 148°–149° C.; ir (CHCl$_3$) 3080, 3000, 1585, 1528, 1440, 1334 cm$^{-1}$; nmr (CDCl$_3$) δ 8.30(s,2), 6.90–8.10(m,8).

Part B: Preparation of 4-(4-[4-chlorophenylsulfonyl]phenoxy)-3,5-dichloroaniline To a 100 mL flask equipped with condenser, stirrer, under nitrogen atmosphere was added 26.9 g. (0.11 mol) of stannous chloride, 23.9 mL of concentrated hydrochloric acid, and 17.9 mL of p-dioxane. The resulting mixture was warmed to 40° to obtain a homogeneous solution. To the above solution was added 16.6 g (0.036 mol) of 4-(4-[4-chlorophenylsulfonyl]phenoxy)-3,5-dichloronitrobenzene. The mixture was heated to reflux for 0.5 hour, cooled, and poured into chilled aqueous sodium hydroxide (pH 14). This mixture was extracted twice with methylene chloride. The combined organic layer was washed successively with aqueous sodium hydroxide, water, and brine. It was then dried over sodium sulfate and was concentrated to give 14.2 g (0.033 mol) of a white solid; mp 186°–187° C.

Anal: C$_{18}$H$_{12}$Cl$_3$NO$_3$S: Calcd: C, 50.43; H, 2.82; N, 3.27. Found C, 50.24; H, 2.77; N, 3.20.

Part C: Preparation of 1-(2,6-Difluorobenzoyl)-3-(3,5-dichloro-4-[4-(4-chlorophenylsulfonyl)phenoxy]phenyl)urea To a 250 mL flask equipped with stirrer, condenser, under nitrogen atmosphere was added 10 g (0.023 mol) of 4-(4-[4-chlorophenylsulfonyl]phenoxy)-3,5-dichloroaniline and 130 mL of toluene. The mixture was heated up to 80° to obtain a clear solution. A solution of 6.82 g of 2,6-difluorobenzoylisocyanate and 4 mL of toluene was added. The resulting mixture was stirred at 80° for 1.5 hours. The reaction mixture was cooled and filtered to give 14.2 g (0.023 mol) of a white solid; mp 207.2°–209.2° C.

Anal: C$_{26}$H$_{15}$Cl$_3$N$_2$O$_5$S: Calcd: C, 54.18; H, 2.62; N, 4.86. Found: C, 52.92; H, 2.80; N, 4.28.

Part D: Preparation of 4-(4-[4-chlorophenylsulfonyl]phenoxy)-2-methylaniline To a 250 mL flask equipped with stirrer, condenser, under nitrogen atmosphere, was added 20 g (0.070 mol) of 4,4'-dichlorodiphenylsulfone, 12.8 g (0.104 mol) of 3-methyl-4-aminophenol, 15.5 g (0.112 mol) of potassium carbonate, and 130 mL of dimethylformamide. The resulting mixture was stirred at room temperature for 24 hours and at 125° for 28 hours. It was cooled and concentrated. The concentrated material was dissolved in 400 mL of toluene and washed with 4% sodium hydroxide, followed by water and brine washes. The organic layer was dried over sodium sulfate, concentrated, and chromatographed through 350 g of florisil column. Elution with hexane/ethylacetate (8/2) afforded 11.2 g (0.030 mol) of a yellow solid; mp 200° D.

Anal: C$_{19}$H$_{16}$ClNO$_3$S: Calcd: C, 62.04; H, 4.31; N, 3.75. Found: C, 61.21; H, 4,42; N, 3.70.

Part E: Preparation of 2,5-dimethyl-3-chloro-4-(4-[4-Chlorobenzoyl]phenoxy)aniline A mixture of 2,5-dimethyl-3-chloro-4-(4-[4-chlorobenzoyl]phenoxy)nitrobenzene (5.95 g, 14 mmol), toluene (160 mL), and 5% platinum on carbon (0.65 g) was subjected to hydrogenation at the pressure ≦24 psi. After 8 h one reaction was found to be partly completed. Additional catalyst (0.2 g of 5% pt/c) was added. The reaction was close to completion by the end of additional 4 h. The mixture was filtered and the filtrate was concentrated to give an amber foam. This foam was dissolved in an ethyl acetate (5 mL) and hexane (10 mL). Solid formed after the addition of seed crystal and vigorous stirring. A tan powder was obtained after filtration (3.93 g); mp 113°–122°. In a similar experiment a buff powder was obtained; IR (CHCl$_3$) 3020, 2405, 1650, 1600 cm$^{-1}$; NMR (CDCl$_3$) δ 6.6–7.8 (M, 8H), 6.5 (S, 1H) 3.5 (br, 2H), 2.2 (S, 3H), 2.1 (S, 3H)

EXAMPLES 1-42

In a manner similar to that employed in the preceding examples, and using one of the synthesis schemes previously disclosed, other urea compounds were prepared. The identity of the substituents on the generic formula and the analytical data are set forth in table I below:

TABLE I
Properties of Benzoyl Ureas

![Generic structure 1: R1,R2-substituted benzoyl-NH-C(O)-NH-phenyl(R3,R4,Y)-O-phenyl-B-phenyl-Cl]

| | | | | | | | | | Calculated | | | Found | | |
|---|---|---|---|---|---|---|---|---|---|---|---|---|---|---|
| Example | Molecular Formula | R1 | R2 | R3 | R4 | Y | B | | C | H | N | C | H | N |
| 1 | $C_{26}H_{15}Cl_5N_2O_5S$ | Cl | Cl | 3-Cl | 5-Cl | C | $SO_2$ | | 48.44 | 2.35 | 4.35 | 47.88 | 2.41 | 4.17 |
| 2 | $C_{26}H_{15}Cl_3F_2N_2O_5S$ | F | F | 3-Cl | 5-Cl | C | $SO_2$ | | 54.18 | 2.62 | 4.86 | 52.92 | 2.80 | 4.28 |
| 3 | $C_{26}H_{16}Cl_2F_2N_2O_5S$ | F | F | 3-Cl | H | C | $SO_2$ | | 54.09 | 2.79 | 4.85 | 53.45 | 2.64 | 4.77 |
| 4 | $C_{26}H_{15}Cl_4F_1N_2O_5S$ | Cl | F | 3-Cl | 5-Cl | C | $SO_2$ | | 49.71 | 2.41 | 4.46 | 52.11 | 2.68 | 4.15 |
| 5 | $C_{26}H_{26}Cl_3F_1N_2O_5S$ | Cl | F | 3-Cl | H | C | $SO_2$ | | 52.59 | 2.72 | 4.72 | 52.33 | 2.68 | 4.65 |
| 6 | $C_{26}H_{16}Cl_4N_2O_5S$ | Cl | H | 3-Cl | 5-Cl | C | $SO_2$ | | *607.9534 | | | *607.9547 | | |
| 7 | $C_{26}H_{17}Cl_1F_2N_2O_5S$ | F | F | H | H | C | $SO_2$ | | 57.52 | 3.16 | 5.16 | 58.35 | 3.27 | 5.11 |
| 8 | $C_{26}H_{18}Cl_2N_2O_5S$ | Cl | H | H | H | C | $SO_2$ | | 57.68 | 3.35 | 5.17 | 58.85 | 3.44 | 5.02 |
| 9 | $C_{26}H_{17}Cl_2F_1N_2O_5S$ | Cl | F | H | H | C | $SO_2$ | | 55.80 | 3.06 | 5.00 | 56.73 | 3.08 | 4.93 |
| 10 | $C_{26}H_{23}Cl_1N_2O_7S$ | $OCH_3$ | $OCH_3$ | H | H | C | $SO_2$ | | 59.31 | 4.09 | 4.94 | 63.52 | 4.25 | 4.80 |
| 11 | $C_{26}H_{18}Cl_1F_2N_3O_5S$ | F | F | 3-$CH_3$ | — | N | $SO_2$ | | 55.97 | 3.25 | 7.53 | 56.28 | 3.22 | 7.43 |
| 12 | $C_{26}H_{18}Cl_2FN_3O_5S$ | Cl | F | 3-$CH_3$ | — | N | $SO_2$ | | 54.37 | 3.16 | 7.32 | 54.57 | 3.15 | 7.30 |
| 13 | $C_{26}H_{28}Cl_3N_3O_5S$ | Cl | Cl | 3-$CH_3$ | — | N | $SO_2$ | | 52.85 | 3.07 | 7.11 | 56.01 | 3.59 | 6.25 |
| 14 | $C_{25}H_{15}Cl_2F_2N_3O_5S$ | F | F | 3-Cl | — | N | $SO_2$ | | 51.92 | 2.61 | 7.27 | 52.12 | 2.43 | 7.37 |
| 15 | $C_{25}H_{15}Cl_3FN_3O_5S$ | Cl | F | 3-Cl | — | N | $SO_2$ | | 50.48 | 2.54 | 7.06 | 50.77 | 2.39 | 7.17 |
| 16 | $C_{25}H_{16}Cl_3N_3O_5S$ | Cl | H | 3-Cl | — | N | $SO_2$ | | 52.06 | 2.86 | 7.28 | 52.30 | 2.65 | 7.32 |
| 17 | $C_{25}H_{16}Cl_1F_2N_3O_5S$ | F | F | H | — | N | $SO_2$ | | 55.20 | 2.97 | 7.73 | 55.12 | 2.83 | 7.72 |
| 18 | $C_{25}H_{16}Cl_2FN_3O_5S$ | Cl | F | H | — | N | $SO_2$ | | 53.58 | 2.88 | 7.50 | 53.39 | 2.79 | 7.60 |
| 19 | $C_{25}H_{16}Cl_3N_3O_5S$ | Cl | Cl | H | — | N | $SO_2$ | | 52.06 | 2.80 | 7.28 | 51.86 | 2.75 | 7.29 |
| 20 | $C_{27}H_{20}Cl_2N_2O_5S$ | Cl | H | 3-$CH_3$ | H | C | $SO_2$ | | 58.39 | 3.63 | 5.04 | 60.28 | 4.07 | 4.79 |
| 21 | $C_{27}H_{19}Cl_2FN_2O_5S$ | Cl | F | 3-$CH_3$ | H | C | $SO_2$ | | 56.55 | 3.34 | 4.89 | 56.50 | 3.40 | 4.87 |
| 22 | $C_{27}H_{29}Cl_1N_2O_5S$ | F | F | 3-$CH_3$ | H | C | $SO_2$ | | 58.23 | 3.44 | 5.03 | 58.20 | 3.44 | 5.01 |
| 23 | $C_{27}H_{19}Cl_3N_2O_5S$ | Cl | Cl | 3-$CH_3$ | H | C | $SO_2$ | | 54.98 | 3.25 | 4.75 | 55.41 | 3.34 | 4.69 |
| 24 | $C_{27}H_{19}ClF_2N_2O_5S$ | F | F | 2-$CH_3$ | H | C | $SO_2$ | | 58.23 | 3.44 | 5.03 | 58.52 | 3.66 | 4.75 |
| 25 | $C_{27}H_{19}Cl_2FN_2O_5S$ | F | Cl | 2-$CH_3$ | H | C | $SO_2$ | | 56.55 | 3.34 | 4.89 | 56.90 | 3.46 | 4.86 |
| 26 | $C_{27}H_{19}Cl_3N_2O_5S$ | Cl | Cl | 2-$CH_3$ | H | C | $SO_2$ | | 54.98 | 3.25 | 4.75 | 55.36 | 3.56 | 4.70 |
| 27 | $C_{27}H_{20}Cl_2N_2O_5S$ | Cl | H | 2-$CH_3$ | H | C | $SO_2$ | | 58.39 | 3.63 | 5.04 | 58.55 | 3.72 | 4.96 |
| 28 | $C_{26}H_{26}Cl_2F_2N_2O_3S$ | F | F | 3-Cl | H | C | S | | 57.26 | 2.96 | 5.14 | 57.00 | 2.85 | 5.21 |
| 29 | $C_{26}H_{16}Cl_3FN_2O_3S$ | Cl | F | 3-Cl | H | C | S | | 55.58 | 2.87 | 4.99 | 55.61 | 2.91 | 4.91 |
| 30 | $C_{26}H_{17}Cl_3N_2O_3S$ | Cl | H | 3-Cl | H | C | S | | 57.42 | 3.15 | 5.15 | 57.35 | 3.12 | 5.12 |
| 31 | $C_{27}H_{19}ClF_2N_2O_3S$ | F | F | 3-$CH_3$ | H | C | S | | 61.77 | 3.65 | 5.34 | 61.55 | 3.57 | 5.43 |
| 32 | $C_{27}H_{19}Cl_2FN_2O_3S$ | Cl | F | 3-$CH_3$ | H | C | S | | 59.90 | 3.54 | 5.17 | 57.64 | 3.50 | 5.59 |
| 33* | $C_{27}H_{20}Cl_2N_2O_3S$ | Cl | H | 3-$CH_3$ | H | C | S | | 61.96 | 3.85 | 5.35 | 61.87 | 3.84 | 5.30 |
| 34 | $C_{28}H_{21}Cl_1F_2N_2O_5S$ | F | F | 2-$CH_3$ | 6-$CH_3$ | C | $SO_2$ | | 58.90 | 3.71 | 4.91 | 58.88 | 3.63 | 4.89 |
| 35 | $C_{28}H_{21}Cl_2FN_2O_5S$ | F | Cl | 2-$CH_3$ | 6-$CH_3$ | C | $SO_2$ | | 56.29 | 3.54 | 4.77 | 57.39 | 3.58 | 4.82 |
| 36 | $C_{28}H_{21}Cl_3N_2O_5S$ | Cl | Cl | 2-$CH_3$ | 6-$CH_3$ | C | $SO_2$ | | 55.69 | 3.50 | 4.64 | 55.57 | 3.42 | 4.72 |
| 37 | $C_{28}H_{22}Cl_2N_2O_5S$ | Cl | H | 2-$CH_3$ | 6-$CH_3$ | C | $SO_2$ | | 59.03 | 3.89 | 4.92 | 58.99 | 3.76 | 5.04 |
| 38 | $C_{26}H_{15}Cl_3F_2N_2O_3S$ | F | F | 3-Cl | 5-Cl | C | S | | 53.86 | 2.61 | 4.83 | 54.04 | 2.56 | 4.93 |
| 39 | $C_{26}H_{15}Cl_4FN_2O_3S$ | Cl | F | 3-Cl | 5-Cl | C | S | | 52.37 | 2.54 | 4.70 | 51.48 | 2.40 | 5.09 |
| 40 | $C_{28}H_{21}Cl_1F_2N_2O_3S$ | F | F | 3-$CH_3$ | 5-$CH_3$ | C | S | | 62.39 | 3.93 | 5.20 | 62.16 | 3.97 | 5.01 |
| 41 | $C_{28}H_{21}Cl_2FN_2O_3S$ | Cl | F | 3-$CH_3$ | 5-$CH_3$ | C | S | | 60.54 | 3.81 | 5.04 | 60.22 | 3.68 | 5.09 |
| 42 | $C_{28}H_{22}Cl_2N_2O_3S$ | Cl | H | 3-$CH_3$ | 5-$CH_3$ | C | S | | 62.57 | 4.17 | 5.21 | 62.50 | 4.01 | 5.21 |

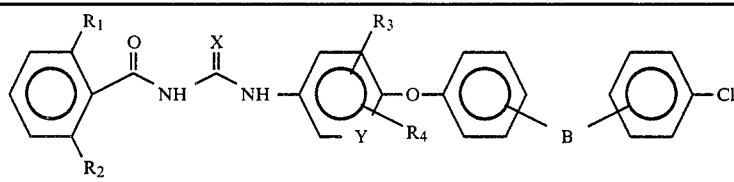

| | | | | | | | | | | Calculated | | | Found | | |
|---|---|---|---|---|---|---|---|---|---|---|---|---|---|---|---|
| Example | Molecular Formula | X | R1 | R2 | R3 | R4 | (1) | Y | B | C | H | N | C | H | N |
| 43 | $C_{28}H_{21}Cl_3N_2O_5S$ | O | Cl | H | 2-$CH_3$ | 5-$CH_3$ | (P) | CCl | $SO_2$ | 55.69 | 3.50 | 4.64 | 55.99 | 3.66 | 4.67 |
| 44 | $C_{28}H_{20}Cl_2F_2N_2O_5S$ | O | F | F | 2-$CH_3$ | 5-$CH_3$ | (P) | CCl | $SO_2$ | 55.55 | 3.33 | 4.63 | 56.60 | 4.42 | 3.74 |
| 45 | $C_{26}H_{18}Cl_2N_2O_5S$ | O | Cl | H | H | H | (M) | CH | $SO_2$ | 57.62 | 3.35 | 5.17 | 58.58 | 3.44 | 5.32 |
| 46 | $C_{26}H_{17}Cl_3N_2O_5S$ | O | Cl | Cl | H | H | (M) | CH | $SO_2$ | 54.22 | 2.98 | 4.86 | 54.44 | 3.02 | 5.02 |
| 47 | $C_{26}H_{17}Cl_2FN_2O_5S$ | O | Cl | F | H | H | (M) | CH | $SO_2$ | 55.70 | 3.27 | 5.00 | 56.26 | 3.10 | 4.99 |
| 48 | $C_{26}H_{17}ClF_2N_2O_5S$ | O | F | F | H | H | (M) | CH | $SO_2$ | 57.51 | 3.16 | 5.16 | 58.54 | 3.31 | 5.06 |
| 49 | $C_{29}H_{20}Cl_2F_2N_2O_4$ | O | F | F | 2-$CH_3$ | 5-$CH_3$ | (P) | CCl | CO | 61.18 | 3.54 | 4.92 | 61.03 | 3.61 | 4.96 |
| 50 | $C_{29}H_{21}Cl_3N_2O_3S$ | S | Cl | H | 2-$CH_3$ | 5-$CH_3$ | (P) | CCl | CO | 59.65 | 3.62 | 4.80 | 59.61 | 3.68 | 5.15 |

TABLE I-continued

Properties of Benzoyl Ureas

| 51 | C$_{29}$H$_{21}$Cl$_3$N$_2$O$_4$ | | O | Cl | H | 2-CH$_3$ | 5-CH$_3$ | (P) | CCl | CO | 61.34 | 3.73 | 4.93 | 61.92 | 4.08 | 4.75 |

*Exact Mass.
(1) Attachment of phenoxy group to phenyl group meta (M) or para (P)

Certain representative examples of the new compounds were evaluated to determine their pesticidal activity against mites and certain insects, including a caterpillar and a beetle. The new compounds were also tested for phytotoxicity on important economic crops including bean, soybean, corn, tomato and cotton. The new compounds were further evaluated for mammalian toxicity.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound.

Certain of the test compounds were also prepared by dissolving 375 mg of compound in 7.5 ml of dimethylformamide. Fifteen ml of acetone containing 37.5 mg (10 percent of the weight of test compound) of an alkylphenoxy polyethoxyethanol surfactant, as a wetting-/emulsifying/dispersing agent was added to the dimethylformamide solution. Fifty-two and a half ml of water was mixed into the dimethylformamide-acetone mixture to give roughly 75 ml of a suspension containing the compound in solution or in finely divided form. The thus prepared stock suspension contained 0.5 percent by weight of compound. The test concentrations in parts per million by weight employed in the tests described hereinbelow were obtained by appropriate dilutions of the stock suspension with water. The test procedures were as follows:

Southern Armyworm Leaf Spray Bait Test

Larvae of the southern armyworm (*Spodoptera eridania*, (Cram.), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestic*, Muls.), reared on Tendergreen bean plants at a temperature of 80°±5° F. and 50±5 percent relative humidity, were the test insects.

For certain of the tests second instar larvae (weighing about 6 mg) of the Mexican bean beetle (*Epilachna varivestis*, Muls), reared on Seiva Pole lima bean plants at a temperature of 80°±5° F. and 5±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead.

Mite Foilage Spray Test

Adults and nymphal stages of the two-spotted mite (*Tetranychus urticae* Koch) reared on Tendergreen beans under controlled conditions (80°+5° F. and 50±5 percent relative humidity). Infested leaves from the stock culture are placed on the primary leaves of 2 bean plants 6-8 inches in height. A sufficient number of mites for testing (150-200) will transfer from the excised leaves to the fresh plants.

Infested Tendergreen bean plants of standard height and age are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to set the plants to run-off.

The test compounds are formulated by a standard procedure of solution in acetone/DMF, addition of an emulsifier, and dilution with water. Primary spray applications are conducted at 500 ppm.

The treated plants are held at 80°±5° F. and 50±5 percent relative humidity for a period of 7 days when mortality counts of motile forms (adults and nymphs) are made.

Microscopic examination of motile forms is made on one leaf from each of the 2 test plants. Any individual which is capable of locomotion upon stimulation is considered living.

Mite Ovicide Test

The egg of the two-spotted mite *Tetranychus uritcae* (Koch) obtained from adults reared on Tendergreen beans under controlled conditions (80°±5° F. and 50±5 percent relative humidity). Heavily infested leaves from the stock culture are placed on uninfested bean plants. Females are allowed to oviposit for a period of 24 hours, and the leaves of the plants are then dipped in an 1000 ppm solution of TEPP in order to kill the motile forms and prevent additional egg laying. TEPP does not affect the viability of the eggs.

The plants are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to set the plants to runoff. An equivalent amount of a water solution containing acetone/DMF and emulsifier in the same concentrations as the insecticidal mixture but without the candidate insecticide is also sprayed on the infested plants as a check or control.

The test compounds are formulated by a standard procedure of solution in acetone, addition of an emulsifier, and dilution with water. Primary screening tests are conducted at 500 ppm.

The treated plants are held at 80°±5° F. and 50±5 percent relative humidity for 7 days after which counts are made.

Microscopic examination is made of the plant leaves, and the number of unhatched eggs (considered dead) and empty egg shells (living eggs) are noted.

The biological properties of certain representative examples of the compounds of this invention are set forth in Table II below.

TABLE II

Biological Properties of Representative Benzoyl Ureas

| | Activity 500 ppm | |
|---|---|---|
| Example | SAW[1] | MBB[2] |
| 1 | A | C |
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 12 | A | A |
| 13 | A | A |
| 14 | A | A |
| 15 | A | A |
| 17 | A | A |
| 18 | A | A |
| 19 | A | A |
| 20 | A | A |
| 21 | A | A |
| 22 | A | A |
| 23 | A | A |
| 24 | A | A |
| 25 | A | A |
| 26 | A | A |
| 27 | A | A |
| 28 | A | A |
| 29 | A | A |
| 30 | A | A |
| 31 | A | A |
| 32 | A | A |

TABLE II-continued

Biological Properties of Representative Benzoyl Ureas

| | Activity 500 ppm | |
|---|---|---|
| Example | SAW[1] | MBB[2] |
| 33 | A | A |
| 34 | A | A |
| 35 | A | A |
| 36 | C | A |
| 37 | C | A |
| 38 | A | A |
| 39 | A | A |
| 40 | A | A |
| 41 | A | A |
| 43 | A | A |
| 44 | A | A |
| 45 | A | A |
| 46 | C | A |
| 47 | A | A |
| 48 | A | A |
| 49 | A | A |

[1]Southern Armyworm
[2]Mexican Bean Beetle
[3]Code =
A = Complete control
B = Moderate control
C = No control

EXAMPLES 43-46

In order to demonstrate the enhanced biological activity against the Southern Armyworm, representative benzoyl ureas were compared with known products. The results are set forth in Table III below:

TABLE III

Comparison Of Representative Benzoyl Ureas With Known Compounds Against Southern Armyworm

| Compound | Application rate (ppm) | Percent Control after 5 days |
|---|---|---|
| 1-(4-chlorophenyl)-3-(2,6-difluorobenzoyl)urea[1] | 10 | 100 |
| | 5 | 40 |
| 1-(2,6-difluorobenzoyl)-3-(3,5-dichloro-4-[4-(4-chloro-phenylsulfonyl)phenoxy]phenyl)urea | 12 | 100 |
| | 6 | 90 |
| | 3 | 100 |
| 1-(2,6-difluorobenzoyl)-3-(3-chloro-4-[4-(4-chloro-phenylsulfonyl)-phenoxy]phenyl)urea | 12 | 100 |
| | 6 | 75 |
| | 3 | 56 |
| 1-(2-chloro-6-fluorobenzoyl)-3-(4-[4-(4-chloro-phenylsulfonyl)phenoxy]-phenyl)urea | 20 | 100 |
| | 6 | 100 |
| | 1.5 | 60 |

[1]Dimilin, a known compound.

EXAMPLES 47-48

In order to demonstrate the enhanced biological activity against Heliothis spp, representative benzoyl ureas were compared with known products. The results are set forth in Table IV below:

TABLE IV

Comparison Of Representative Benzoyl Ureas With Known Compounds Against Heliothis spp

| | LD$_{50}$ (ppm) | |
|---|---|---|
| Compound | H. Zea | H. Virecens |
| 1-(4-chlorophenyl)-3-(2,6-difluorobenzoyl)urea[1] | 500 | 31 |
| 1-(2,6-difluorobenzoyl)-3-(3,5-dichloro-4-[4-((4-chloro-phenylsulfonyl))phenoxy]phenyl)urea | 12.5 | 8.5 |
| 1-(2,6-difluorobenzoyl)-3- | 31 | 31 |

TABLE IV-continued
Comparison Of Representative Benzoyl Ureas With Known Compounds Against Heliothis spp

| Compound | LD$_{50}$ (ppm) | |
|---|---|---|
| | H. Zea | H. Virecens |
| (3-chloro-4-[4-((4-chloro-phenylsulfonyl))-phenoxy]phenyl)urea | | |

[1] Dimilin, a known compound

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. A compound of the formula:

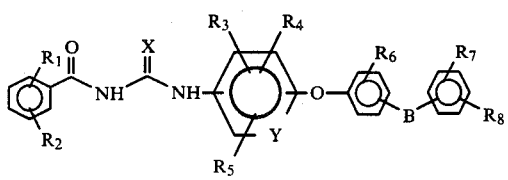

wherein:
X is oxygen or sulfur;
Y is CR$_3$;
B is oxygen, sulfur, sulfinyl, sulfonyl, oxysulfonyl, sulfonyloxy or carbonyl;
R$_1$ and R$_2$ are independently hydrogen, halogen, methoxy, alkyl (C$_1$-C$_4$) or trifluoromethyl;
R$_3$, R$_4$, R$_5$ are independently hydrogen, methoxy, halogen, alkyl (C$_1$-C$_4$) or trifluoromethyl;
R$_6$ is hydrogen, halogen or alkyl (C$_1$-C$_4$) or trifluoromethyl; R$_7$, R$_8$ are independently hydrogen, halogen, alkyl (C$_1$-C$_4$), trifluoromethyl, alkylthio (C$_1$-C$_4$), alkylsulfinyl (C$_1$-C$_4$), alkylsulfonyl (C$_1$-C$_4$), or R$_7$ and R$_8$ can optionally be a substituted arylthio, a substituted arylsulfonyl, or a substituted arylsulfinyl, wherein said optional substituents are alkyl (C$_1$-C$_4$) or halogen and provided that when B is oxygen, and Y is CR$_3$, at least two of R$_3$-R$_5$ are other than hydrogen.

2. The compound of claim 1 which has the formula:

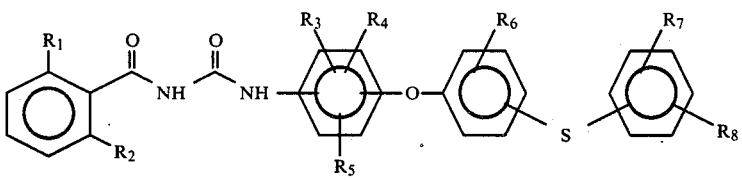

wherein:
B is oxygen, sulfur, sulfinyl, sulfonyl, oxysulfonyl, sulfonyloxy or carbonyl;
R$_1$ and R$_2$ are independently hydrogen, halogen methoxy, alkyl (C$_1$-C$_4$) or trifluoromethyl;
R$_3$, R$_4$ and R$_5$ are independently hydrogen, halogen, methoxy, alkyl (C$_1$-C$_4$) or trifluoromethyl;
R$_6$ is hydrogen, halogen or alkyl (C$_1$-C$_4$) or trifluoromethyl;
R$_7$, R$_8$ are independently hydrogen, halogen, alkyl (C$_1$-C$_4$), trifluoromethyl, alkylthio (C$_1$-C$_4$), alkylsulfinyl (C$_1$-C$_4$), alkylsulfonyl (C$_1$-C$_4$), or R$_7$ and R$_8$ can optionally be a substituted arylthio, a substituted arylsulfonyl, or a substituted arylsulfonyl, provided that when B is oxygen, and Y is CR$_3$, at least two of R$_3$-R$_5$ are other than hydrogen.

3. The compound of claim 1 which has the formula:

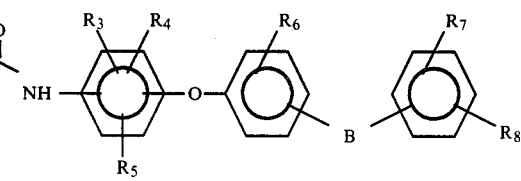

wherein:
R$_1$ and R$_2$ are independently hydrogen, halogen, methoxy, alkyl (C$_1$-C$_4$) or trifluoromethyl;
R$_3$, R$_4$, R$_5$ are independently hydrogen, methoxy, halogen, alkyl, (C$_1$-C$_4$) or, trifluoromethyl;
R$_6$ is hydrogen, halogen or alkyl (C$_1$-C$_4$), or trifluoromethyl;
R$_7$, R$_8$ are independently hydrogen, halogen, alkyl (C$_1$-C$_4$), trifluoromethyl, alkylthio (C$_1$-C$_4$), alkylsulfinyl (C$_1$-C$_4$), alkylsulfonyl (C$_1$-C$_4$), or R$_7$ and R$_8$ can optionally be a substituted arylthio, a substituted arylsulfonyl, or a substituted arylsulfinyl.

4. The compound of claim 1 which has the formula:

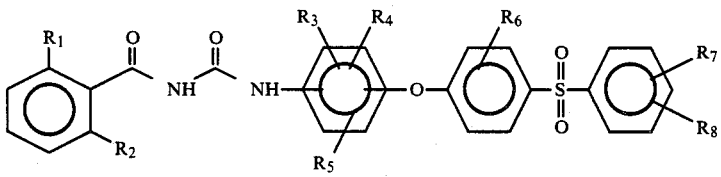

wherein $R_1$ and $R_2$ are independently hydrogen, halogen, methoxy, alkyl ($C_1$-$C_4$) or trifluoromethyl;

$R_3$, $R_4$, $R_5$ are independently hydrogen, methoxy, halogen, alkyl, ($C_1$-$C_4$) trifluoromethyl;

$R_6$ is hydrogen, halogen or alkyl ($C_1$-$C_4$), or trifluoromethyl;

$R_7$, $R_8$ are independently hydrogen, halogen, alkyl ($C_1$-$C_4$), trifluoromethyl, alkylthio ($C_1$-$C_4$), alkylsulfinyl ($C_1$-$C_4$), alkylsulfonyl ($C_1$-$C_4$), or $R_7$ and $R_8$ can optionally be a substituted arylthio, a substituted arylsulfonyl, or a substituted arylsulfinyl.

5. The compound of claim 1 which has the formula:

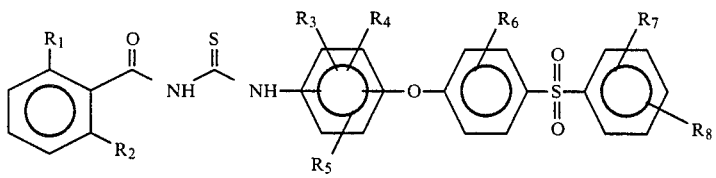

wherein:

$R_1$ and $R_2$ are independently hydrogen, halogen, methoxy, alkyl ($C_1$-$C_4$) or trifluoromethyl;

$R_3$, $R_4$, $R_5$ are independently hydrogen, methoxy, halogen, alkyl ($C_1$-$C_4$);

$R_6$ is hydrogen, halogen or alkyl ($C_1$-$C_4$), or trifluoromethyl;

$R_7$, $R_8$ are independently hydrogen, halogen, alkyl ($C_1$-$C_4$), trifluoromethyl, alkylthio ($C_1$-$C_4$), alkylsulfinyl ($C_1$-$C_4$), alkylsulfonyl ($C_1$-$C_4$), or $R_7$ and $R_8$ can optionally be a substituted arylthio, a substituted arylsulfonyl, or a substituted arylsulfinyl.

6. The compound of claim 1 which is 1-(2,6-difluorobenzoyl)-3-(3,5-dichloro-4-[4-(4-chlorophenylsulfonyl)phenoxy]phenyl)urea.

7. The compound of claim 1 which is 1-(2,6-difluorobenzoyl)-3-(3-chloro-4-[4-(4-chlorophenylsulfonyl)phenoxy]phenyl)urea.

8. The compound of claim 1 which is 1-(2-chloro-6-fluorobenzoyl)-3-(4-[4-(4-chlorophenylsulfonyl)phenoxy]phenyl)urea.

9. The compound of claim 1 which is 1-(2.6-difluorobenzoyl)-3-(3-methyl-4-[4-(4-chlorophenylsulfonyl)phenoxy]phenyl)urea.

10. The compound of claim 1 which is 1-(2,6-difluorobenzoyl)-3-(2-methyl-4-[4-(4-chlorophenylsulfonyl)phenoxy]phenyl)urea.

11. The compound of claim 1 which is 1-(2,6-difluorobenzoyl)-3-(3-chloro-4-[4-(4-chlorophenylsulfenyl)phenoxy]phenyl)urea.

12. The compound of claim 1 which is 1-(2,6-difluorobenzoyl)-3-(2,6-dimethyl-4-[4-(4-chlorophenylsulfonyl)phenoxy]phenyl)urea.

13. The compound of claim 1 which is 1-(2,6-difluorobenzoyl)-3-[4-(4-chlorophenylsulfonyl)phenoxy]phenyl)urea.

14. The compound of claim 1 which is 1-(2,6-difluorobenzoyl)-3-(2,5-dimethyl-3-chloro-4-[4-(4-chlorophenylsulfonyl)phenoxy]phenyl)urea.

15. The compound of claim 1 which is 1-(2,6difluorobenzoyl)-3-(3-methyl-4-[4-(4-chlorophenylsulfenyl)phenoxy]phenyl)urea.

16. The compound of claim 1 which is 1-(2,6-difluorobenzoyl)-3-(2,5-dimethyl-3-chloro-4-[4-(4-chlorobenzoyl)phenoxy]phenyl)urea.

17. The compound of claim 1 which is 1-(2-chlorobenzoyl)-3-(2,5-dimethyl-3-chloro-4-[4-(4-chlorobenzoyl)phenoxy]phenyl)thiourea.

18. A pesticide composition comprising an acceptable carrier and a pesticidally effective amount of the compound of claim 1.

19. A pesticide composition comprising an acceptable carrier and a pesticidally effective amount of the compound of claim 2.

20. A pesticide composition comprising an acceptable carrier and a pesticidally effective amount of the compound of claim 4.

21. A pesticide composition comprising an acceptable carrier and a pesticidally effective amount of the compound of claim 5.

22. A pesticide composition comprising an acceptable carrier and a pesticidally effective amount of the compound of claim 7.

* * * * *